United States Patent [19]
D'Silva

[11] Patent Number: 5,033,541
[45] Date of Patent: Jul. 23, 1991

[54] DOUBLE PASS TANDEM COOLING AEROSOL CONDENSER

[75] Inventor: Arthur P. D'Silva, Ames, Iowa

[73] Assignee: Cetac Technologies, Inc., Omaha, Nebr.

[21] Appl. No.: 438,779

[22] Filed: Nov. 17, 1989

[51] Int. Cl.$^5$ .............................................. F28D 7/10
[52] U.S. Cl. ..................... 165/155; 165/114; 165/154
[58] Field of Search ................ 165/111, 114, 154, 155

[56] References Cited

U.S. PATENT DOCUMENTS

| | | | |
|---|---|---|---|
| 153,764 | 8/1874 | Frykberg | 165/155 |
| 1,439,274 | 12/1922 | Stalmann | 165/155 |
| 2,218,097 | 10/1940 | Rhodes | 165/155 |
| 2,372,079 | 3/1945 | Gunter | 165/155 X |
| 2,425,669 | 8/1947 | Brock | 165/111 |
| 4,109,863 | 8/1978 | Olson et al. | 239/102 |
| 4,575,609 | 3/1986 | Fassel et al. | 239/424.5 X |
| 4,586,368 | 5/1986 | Rice et al. | 73/23.1 |

FOREIGN PATENT DOCUMENTS

| | | | |
|---|---|---|---|
| 21924 | 1/1905 | Austria | 165/155 |
| 758810 | 12/1903 | France | 165/155 |

OTHER PUBLICATIONS

"Ultrasonic Nebulization of Liq. Samp. for Analytical Induct. Coupled Plasma-Atomic Spectroscopy: an Update", V. Fassel et al.; Spectrochim. Acta; 41B (1986).

Primary Examiner—Allen J. Flanigan
Attorney, Agent, or Firm—Litman, McMahon & Brown

[57] ABSTRACT

A double pass tandem cooling aerosol condenser apparatus for receiving aerosol from a liquid solution for a specimen sample which has been prepared for injection into an inductively coupled plasma associated with an emission spectra or mass spectrometer comprises inner and outer compartments for circulating a coolant therethrough. The aerosol, comprising solvent and analyte particles, is passed through compartments of the condenser which are interposed between the inner and outer coolant compartment. The temperature of the aerosol compartment is adjusted and controlled such that the solvent particles, which would otherwise quench the inductively coupled plasma, are condensed and stripped from the aerosol leaving a relatively stable, dry aerosol containing the desolvated analyte particles for spectrometric analysis.

3 Claims, 2 Drawing Sheets

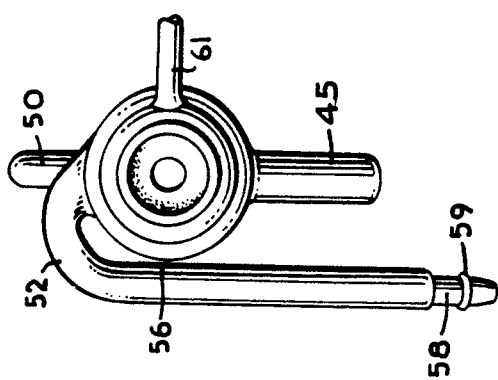
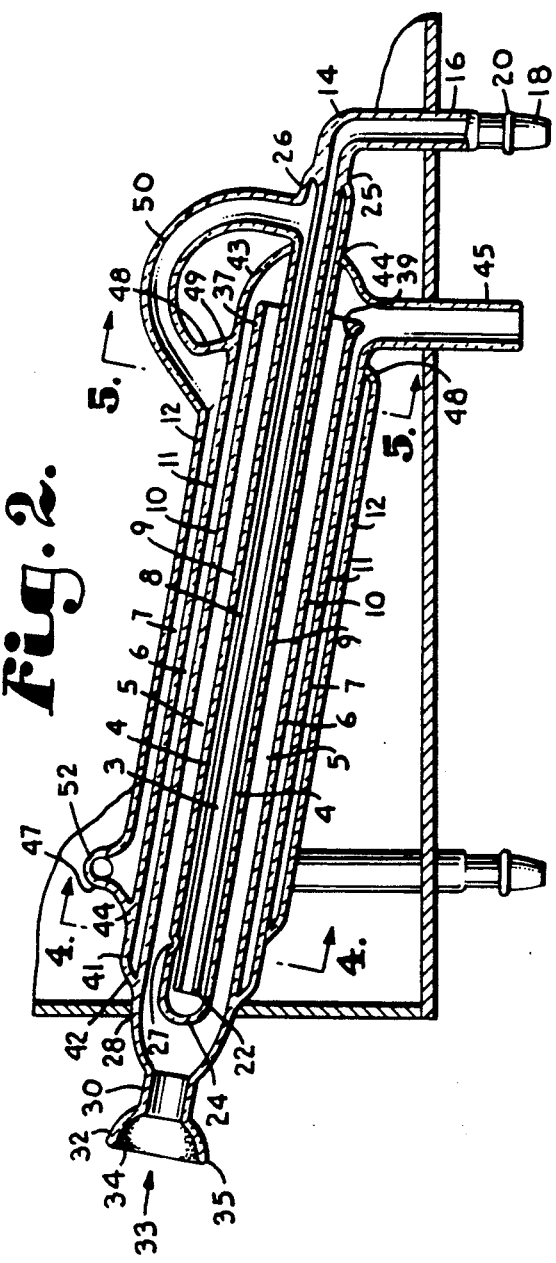
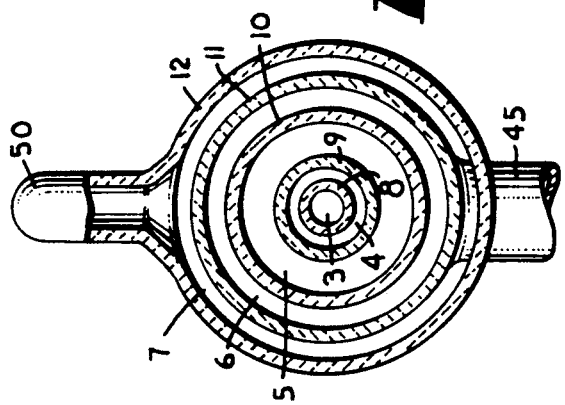
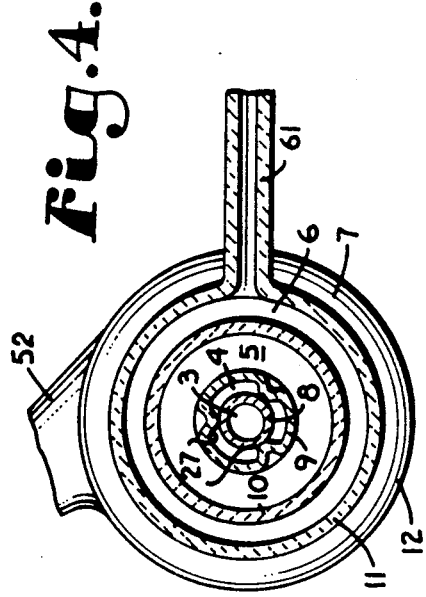

DOUBLE PASS TANDEM COOLING AEROSOL CONDENSER

FIELD OF THE INVENTION

The present application relates to a double-pass double-coolant aerosol condenser apparatus and process for desolvating analyte particle samples prior to introduction of same into laboratory analysis instruments, such as atomic emission or mass spectrometers.

BACKGROUND OF THE INVENTION

Inductively coupled plasma atomic emission spectrometry ("ICP-AES") and inductively coupled plasma mass spectrometry ("ICP-MS") are elemental analysis techniques widely utilized throughout the world. Although ICP-MS instrumentation is of relatively recent origin, the use of this technique is gaining rapidly since significantly superior detection limits can be achieved with ICP-MS over those obtainable with ICP-AES. Both techniques rely on the ability to convert liquid samples into a form which is compatible with an inductively coupled plasma ("ICP"), which is the final component of the techniques just prior to the analysis provided by the spectrometer.

The ICP, which is effectively a high temperature source with effective temperatures ranging from 7,000 K to 10,000 K at various zones within the plasma, is basically used as a torch. The torch serves as a source for either generating excited atomic particles for emission spectra or ions for mass analysis. Sample introduction into the ICP is considered the problematic step associated with these techniques.

The most common technique for introducing liquid samples is as aerosols produced by pneumatic nebulizers. Although there are several designs of pneumatic nebulizers, these only have efficiencies of approximately 1-2 percent with the particles in the resulting aerosol having an average diameter of 10-20 microns. Prior to introduction of the aerosol into the plasma, the aerosol must be subjected to several processes before atomic emission and ionization is observable.

Since the solvent which was utilized to generate the liquid sample will unnecessarily cool the plasma and thus reduce the efficiency of the plasma to produce excitation and ionization, the aerosol preferably should undergo desolation, which strips the solvent from the sample aerosol particles leaving behind a dry aerosol. Following desolvation, the dry aerosol is vaporized in the ICP torch to produce free excited atoms and ions. The vaporization process is inherently affected by the size of the aerosol particles; the smaller the aerosol particles, the more efficient the vaporization process.

Relatively recently, a more efficient nebulizing system in the form of an ultrasonic nebulizer ("USN") has been developed. An USN generally satisfies most of the criteria required for improving the aerosol producing stage of the sample introduction system of an ICP-AES or an ICP-MS. Typically, an USN system has an efficiency of greater than 10 percent and produces an aerosol of particles having sizes ranging from one to three microns in diameter. Unfortunately, the higher efficiency of an USN introduces substantially more solvent into the aerosol with resultant degradation of plasma performance due to cooling, thereby increasing the need for a more efficient desolvation system.

In accordance with the present invention, a desolvation system for aqueous or organic solvents comprises a condenser and preferably a low temperature furnace assembly and one or more condensers connected in series. The furnace is normally operated at a temperature which is sufficient to rapidly convert all suspended liquid particles into vapors. The sample vapors exiting the furnace are directed into the condensers, the number of the condensers depending on the solvent or solvent mixture being analyzed. The function of the condenser is to rapidly strip the solvent vapors from the aerosol stream. To accomplish this goal, the condensers must be maintained at temperatures ranging between $-100°$ C. and $0°$ C., depending on the solvent.

Prior systems have been developed to remove solvent from the sample stream; however, these systems have not been sufficiently effective to consistently produce a relatively solvent-free dry sample to be delivered to the plasma generating region. Such a prior art system is described in the paper by Fassel and Bear entitled "Ultrasonic Nebulization of Liquid Samples for Analytical Inductively Coupled Plasma-atomic Spectroscopy: an Update"; published in *Spectrochim Acta*, Vol. 41B, No. 10, pages 1089 through 1113, 1986, which is incorporated herein by reference to further illustrate overall systems.

The major problem with prior art systems has been the failure of the condenser to perform as needed within the system. Several criteria must be met when designing a practical and high performance condenser, such as (1) providing a compact physical size for the condenser; (2) rapidly cooling the aerosol to minimize nucleation of the desolvated analyte particles with the solvent particles; (3) providing an aerosol flow which is laminar or which has minimal turbulence in order to minimize the nucleation or coalescing of small desolvated analyte particles into larger particles; and (4) rapidly removing the condensed solvent from the condenser in order to prevent reintrainment of solvent vapors in the carrier gas. The present invention is designed to satisfy the above criteria.

SUMMARY OF THE INVENTION

An improved aerosol condenser in accordance with the present invention is provided for use with aerosol samples suspended in a solvent that is preferably aqueous, but may be organic, etc. In an application of the present invention, coolant from a closed cycle cooler initially enters a centrally spaced cold finger. After traversing the length of the finger, the directional flow of the coolant reverses, with the coolant flowing back along a peripheral surface of the cold finger. The coolant that has flowed through the cold finger is then reintroduced about an outer jacket or envelope of the condenser for further cooling of the contents of the condenser. The coolant temperature is preferably maintained in a range between $-10°$ C. and $0°$ C. where the solvent is aqueous.

The liquid sample (including a component to be analyzed and a solvent for the component) is pumped into an aircooled, ultrasonic nebulizer which converts a portion of the sample into an aerosol (component and solvent). Argon gas routed through the nebulizer carries the aerosol into a low temperature furnace which vaporizes the nebulized particles. The aerosol exiting the low temperature furnace enters the condenser and courses through a compartment which surrounds the envelope containing the coolant which is reverse flowing along the central finger. After substantially traversing the length of the condenser, the directional flow of the aerosol reverses, with the aerosol returning in an envelope or compartment which is adjacent to the outer jacket containing the coolant.

The vapors of the solvent condense on the surfaces between the aerosol chambers and the adjacent coolant chambers. The substantially cylindrical peripheral boundaries of the various chambers are canted or positioned such that, during use, the condensed solvent vapors, as they accummulate on the various compartment surfaces, tend to gravitate toward the lower end thereof and subsequently spill into a drain where the condensate is removed from the condenser. The condensed solvent vapors are removed through a liquid trap containing the condensate to avoid contaminating the aerosol environment inside the condenser. To enhance cooling efficiency, the condenser is preferably completely enclosed in a thermally insulated enclosure.

After the aerosol completes the traverses of the two courses or passes within the condenser as aforesaid, the aerosol exits the condenser as a dry aerosol, ready for injection into the plasma of the spectrometer.

To increase the cooling efficiency of the aerosol, one or more additional condensers can be added in series.

OBJECTS OF THE INVENTION

Therefore, the objects of the present invention are: to provide an apparatus which has a compact physical size; to provide such an apparatus that rapidly cools an aerosol to minimize nucleatior of desolvated analyte particles with solvent particles; to provide such an apparatus that produces an aerosol flow which has minimal turbulence in order to minimize the nucleation or coalescing of small desolvated analyte particles into larger particles; to provide such an apparatus that rapidly and substantially removes condensed solvent from the condenser in order to prevent reintrainment of solvent vapors into the carrier gas; to provide such an apparatus that produces a dry aerosol which minimizes or eliminates quenching of an inductively coupled plasma into which the aerosol is injected; and to generally provide an apparatus which is relatively easy to use, simple to maintain, easy to operate efficiently and reliably, and which generally performs the requirements of its intended purposes.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is a vertical cross-sectional view of the apparatus, taken along line 2—2 of FIG. 1.

FIG. 3 is a front elevational view of the apparatus.

FIG. 4 is an enlarged cross-sectional view of the apparatus, taken along line 4—4 of FIG. 2.

FIG. 5 is an enlarged cross-sectional view of the apparatus, taken along line 5—5 of FIG. 2.

DETAILED DESCRIPTION OF THE INVENTION

Figure 1:
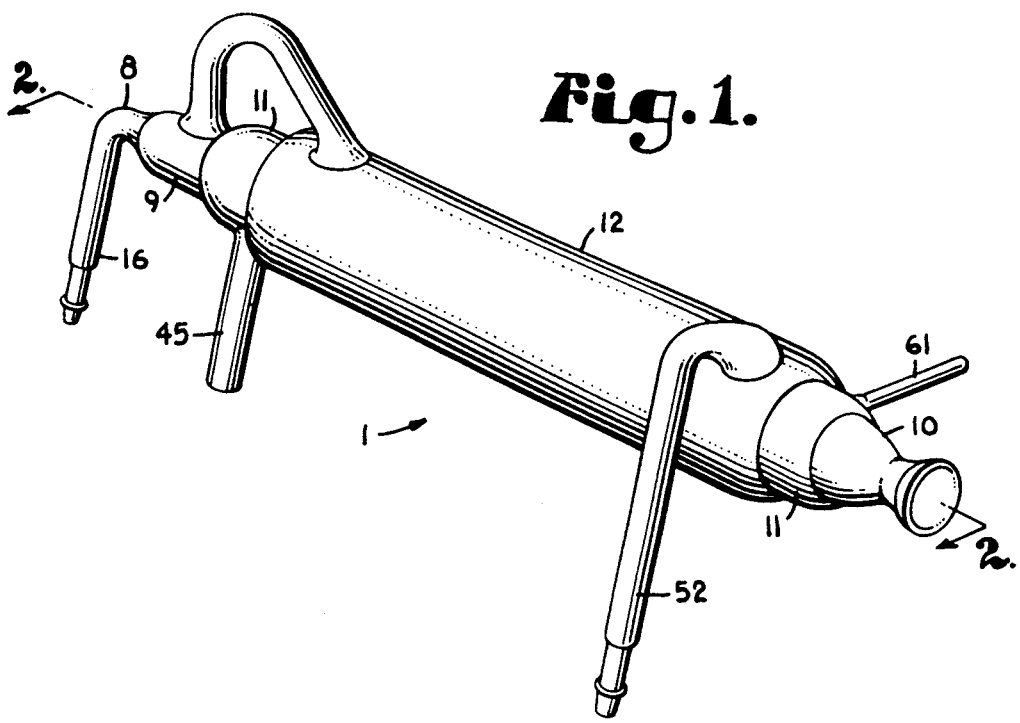
FIG. 1 is a perspective view of a double pass tandem coolant aerosol condenser apparatus in accordance with the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally refers to a double pass tandem cooling aerosol condenser apparatus in accordance with the present invention. The aerosol apparatus is constructed of suitable materials such as glass (for example, such as is sold under the trademark Pyrex) or the like and comprises five concentrically aligned, substantially tubularly shaped compartments 3,4,5,6, and 7, as shown in FIG. 2 which are formed between or within a series of five cylindrically shaped tubes 8,9,10,11 and 12, having progressively larger diameters. The various components of the condenser apparatus 1 are formed and fitted together in a manner well-known in the art of glassblowing.

The tube 8, which is the innermost tube and which contains compartment 3, is bent at an elbow 14 to form a coolant influent port 16. The axis of a coolant influent port 16 forms an angle of slightly greater than 90° with the axis of the tube 8. The coolant influent port 16 has a distal end 18 which is narrowed, with an annular rib 20 to facilitate the telescoping and securement of a section of flexible tubing (not shown) or the like thereabout. The tube 8 is open ended at both the input port 16 and an upper end 22 thereof.

The tube 9, which has a closed end 24, surrounds the tube 8 such that the open upper end 22 of the tube 8 is in close proximity to the closed end 24 of tube 9. An opposite end 26 of tube 9 is formed and bonded to the tube 8 in close proximity to the elbow 14 to form a fluid-tight bond 25 therebetween. A plurality of indentations 27 maintain the end 22 of the tube 8 in substantially centered relationship with the end 24 of the tube 9.

An upper end 28 of the tube 10 narrows into a neck 30 just prior to forming a concave, spherically shaped, enlarged end 32 (socket for glass ball and socket connector), comprising an aerosol input port 33, having an inner surface 34, which is ground to provide gas-tight communication with a convex spherically shaped connector (not shown). A lip 35 is provided to facilitate securement of the concave end 32 to form the gas-tight relationship. The tube 10 surrounds the tube 9. An opposite end 37 of the tube 10 is open and has a lip 39 at a lower extremity thereof.

An upper end 41 of the tube 11, which surrounds the tube 10, is formed and bonded to the tube 10 in close proximity to the closed end 24 of the tube 9 such that a gas-tight bond 42 is formed between the tubes 10 and 11. An opposite end 43 of the tube 11 is formed and bonded to the tube 9 to form a gas-tight bond 44 therebetween. The bond 44 also fixes the spacing of the tube 10 relative to the tube 9. The open end 37 of the tube 10 is contained within the tube 11.

A drain tube 45 is bonded to the tube 11 such that the drain tube 45 flow communicates with the compartments 5 and 6 contained within tubes 10 and 11. The drain tube 45 is substantially parallel to the input end 16 of the tube 8 and is spaced such that the lip 39 is operably positioned directly thereabove.

An upper end 47 of the tube 12, which surrounds the tube 11, is formed and bonded to the tube 11, near the bond 42 between the upper end 41 of the tube 11 and the tube 10, such that a fluid-tight bond 44 is formed therebetween. A lower end 48 of the tube 12 is also formed and bonded to the tube 11, near the bond between the drain tube 45 and the tube 11, such that a fluid-tight bond 49 is formed therebetween.

An arcuate tandem tube 50 is formed and bonded to the tube 9 between the bonds 25 and 44 and to the tube 12 in close proximity to the bond 49 such that the compartment 4 flow communicates with the compartment 7. The tandem tube 50 also serves to structurally reinforce the spaced relationship between the tubes 9 and 10 as established by the bond 44.

A coolant effluent tube 52 is formed and bonded to an upper extremity of the upper end 47 of the tube 12. The effluent tube 52 is arcuately formed and spaced such that a lower portion 54 thereof is substantially parallel to the drain tube 45 and substantially tangential to the tube 12. A bond 56 between the tube 52 and the tube 12 provides structural support for the tube 52.

The tube 52 has a distal end 58 which is narrowed, with an annular rib 59 to facilitate the telescoping and securement of a section of flexible tubing (not shown) thereabout. The tube 52 is adapted to flow communicate with the compartment 7.

An aerosol output port 61 is formed and bonded to the tube 11 between the bonds 42 and 44 such that the port 61 flow communicates with the compartment 6. The port 61 may have any desired orientation. For example, the port 61 may be oriented substantially horizontally during use, such as is shown in FIG. 3.

The thicknesses of the various tubing hereinbefore described must be appropriate to withstand the temperature differentials which exist during use of the apparatus 1 as hereinafter described.

Prior to use of the present invention in conjunction with an aerosol, the condenser 1 is cooled to a desired temperature by pumping a coolant 77, such as methanol or ethylene glycol or any other suitable coolant, through the condenser 1. The coolant 77 is introduced into the condenser 1 through the coolant influent port 16. Upon entering the condenser 1, the coolant 77 flows through the compartment 3 traveling substantially the entire length of the condenser 1. Upon emerging through the open end 22 of the tube 8, the coolant 77 reverses its directional flow and passes through the compartment 4 where the coolant 77 enters the tandem tube 50 and flows into the compartment 7. After traversing the compart 7, the coolant exits the condenser 1 through the coolant effluent port 52 to be transported to an external cooler (not shown) for subsequent cooling to allow repetitive cycling through the condenser 1.

Figure 6:
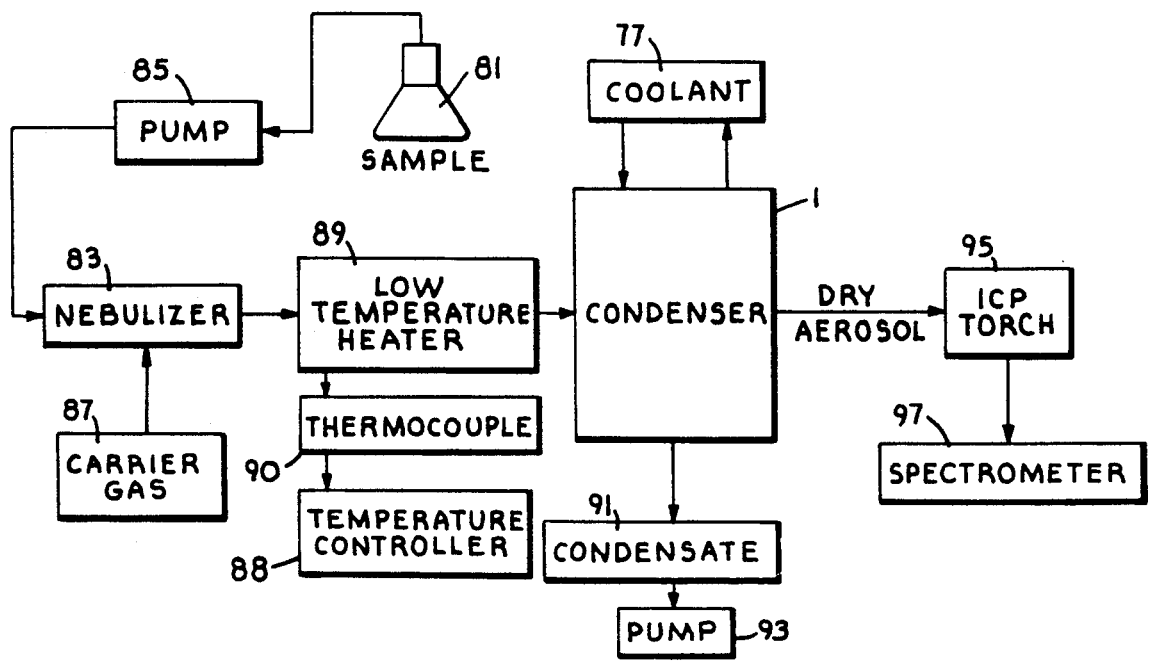
FIG. 6 is a schematic diagram of the aerosol condenser apparatus in accordance with the present invention.

To process an aerosol sample through the condenser 1, a liquid (preferably aqueous) solution 81 of the test specimen is prepared by known methods (see FIG. 6). If the sample is initially in solid form, the sample is first placed into solution, such as with hydrochloric acid, sulphuric acid or the like and diluted such that the solution contains approximately one percent solids or less. The sample solution 81 is then forced into a nebulizer 83 through a pump 85, such as a peristaltic pump, that is flow communicating with the sample solution 81.

As the solution 81 is being nebulized into an aerosol in the nebulizer 83, a carrier gas 87, such as argon or other suitable gas, is coursed through the nebulizer 83 sweeping the aerosol (including components or components to be analyzed and solvent therefor) into a low temperature heater 89. The carrier gas 87 is provided at a flow rate of approximately 1 liter/minute for typical systems, but the actual volume is not critical as long as the flow remains positive.

The operational temperature of the heater 89 is dependent upon the solvent used to form the solution 81. For an aqueous solution, the heater 89 is maintained at a temperature of approximately 140° C. Although water boils at 100° C. at standard pressure, argon gas which also flows through the heater 89 to carry the aerosol to an ICP torch 95 has a cooling effect on the heater 89. Therefore, the heater 89 is preferably maintained at a temperature which is somewhat greater than the boiling point of water to compensate for this cooling effect.

The temperature needed for an organic solvent depends on the identity of the organic solvent. For example, when ethanol, which boils at 78° C. at standard pressure, is used as the solvent, the heater can be operated at a lower temperature, such as 100° C. For mixed liquids, such as ethanol mixed with water, the temperature is adjusted to accommodate the component having the greater boiling point or the boiling of the azeotropic mixture, as necessary. In so doing, however, care must be exercised to avoid decomposing the organic component at the higher temperature. The temperature of the heater 89 is usually maintained within ±0.1° C. of the desired temperature.

The heater 89 usually consists of a quartz tube having an outside diameter of approximately 12 mm and a length of approximately 20 cm. Nichrome wire, which is wound on the peripheral surface thereof, serves as a heating element. The temperature of the aerosol in the quartz tube is measured and controlled with a temperature controller 88 operated through a thermocouple 90. The tip of the thermocouple 90 is positioned at the exit end of the quartz tube.

After being directed through the heater 89, the aerosol is directed into the condenser 1. The aerosol is introduced into the condenser 1 through the aerosol input port 33. The spacing between the heater 89 and the input port 33 is preferably relatively short, such as less than ½ inch. Upon entering the condenser 1, the aerosol impinges upon the closed end 44 of the tube 9 and flows through the compartment 5 which surrounds the tube 9. The tube 9, which contains the coolant 77 therein, serves as a "cold finger", rapidly cooling the aerosol as it flows therealong. Upon emerging through the open end 37 of the tube 10, the aerosol reverses its directional flow and passes through the compartment 6 such that the aerosol essentially makes a double pass through the condenser 1. As the aerosol passes through the compartment 6, the aerosol is in intimate contact with the tube 11 which forms one wall of the compartment 7 and which also contains the coolant 77. Thus, the aerosol experiences further cooling on the second pass.

As the aerosol traverses the compartments 5 and 6, the solvent vapor collects as a condensate 91 on the outside surface of the tube 9, the inside and outside surfaces of the tube 10, and the inside surface of the tube 11. Since the condenser 1 is canted or the tubes angled relative to the horizontal during use such as is shown in FIG. 2, the condensate 91 which collects on the tube 9 gravitates to the bond 44 between the tubes 9 and 11 where the condensate 91 then flows downward along the inner surface of the tube 11 and into the drain port 45. The condensate 91 which collects on the tube 10 gravitates to the open end 37 where it drips from the lip 39 into the drain tube 45. The condensate 91 which collects on the tube 11 gravitates along the inner surface of the tube 11 to the drain port 45.

A flexible tube (not shown), which is attached to the distal end of the drain port 45, is slightly elevated so as to provide a "trap" formed by a small quantity of the condensate 91 therein so as to prevent contaminants from entering the aerosol through the drain port 45. A peristaltic pump 93 aspirates the excess condensate 91 which is not required to perform the trapping function.

After the condenser 1 substantially strips the solvent from the aerosol as the aerosol passes through the chambers 5 and 6, the aerosol, which is then substantially a dry aerosol, exits the condenser 1 through the aerosol output port 61. The dry aerosol, which is relatively stable and which contains the component or components to be analyzed, can be transported over a sizeable distance through a flexible tube (not shown) connected to the output port 61. In one use of the present invention, the dry aerosol was successfully transported through a tube which was approximately five feet in length.

Finally, the dry aerosol is directed into the ICP torch 95 where the dry aerosol is vaporized into free atoms and ions of the sample component. If the analysis is to be performed with an associated spectrometer 97 of the ICP-AES type, the emitted spectra from the elemental atoms which are excited in the ICP torch 95 is analyzed. If the associated spectrometer 97 is of the ICP-MS type, the masses of the elemental ions generated in the ICP torch 95 are analyzed.

It is to be understood that while certain forms of the present invention have been illustrated and described herein, it is not to be limited to the specific forms or arrangement of parts described and shown.

What is claimed and desired to be secured by Letters Patent is as follows:

1. In a condensing apparatus for removing solvent vapor from an aerosol carrying analyte particles of a component to be analyzed prior to introduction thereof into an inductively coupled plasma for speciation spectrometric determination and including cooling means for reducing the temperature of said aerosol, the improvement comprising:
    (a) said cooling means comprising a condenser having a first pair of generally parallel flow connecting compartments adapted to receive said aerosol and to conduct said aerosol with minimal transit time and minimal turbulence therethrough and having a second pair of generally parallel flow connecting compartments; said first pair of compartments sandwiched between said second pair of compartments so as to condense solvent from the aerosol;
    (b) said condensing apparatus is a compartmentalized container constructed from glass;
    (c) said cooling means is a coolant which is circulated through said second pair of compartments; and
    (d) said second pair of compartments includes a finger having a tip; said finger extending substantially through said first pair of compartments such that aerosol entering said first pair of compartments substantially immediately impinges on said cold finger tip.

2. The condensing apparatus according to claim 1 including:
    (a) an arcuate tube for flow connecting said second pair of compartments near a respective end of each compartment; said arcuate tube spaced intermediate said second pair of compartments.

3. The condensing apparatus according to claim 2 wherein:
    (a) said arcuate tube provides structural reinforcement for said cold finger.

* * * * *